US00PP07807P

United States Patent [19]

Fleming

[11] Patent Number: Plant 7,807

[45] Date of Patent: Feb. 25, 1992

[54] KALANCHOE PLANT NAMED MANDARIN

[75] Inventor: Margaret M. Fleming, Soquel, Calif.

[73] Assignee: The Plant Company, Soquel, Calif.

[21] Appl. No.: 606,843

[22] Filed: Oct. 31, 1990

[51] Int. Cl.[5] ..... A01H 5/00
[52] U.S. Cl. ..... Plt./68
[58] Field of Search ..... Plt./68

*Primary Examiner*—James R. Feyrer
*Attorney, Agent, or Firm*—Foley & Lardner

[57] ABSTRACT

A Kalanchoe plant named Mandarin particularly characterized by its pumpkin-orange flower color; flower diameter of up to 18 mm at maturity; flowering response, from 9 weeks in summer to 11 weeks in winter after start of short days; very floriferous, with excellent display of many flowers; good keeping quality of both flowers and foliage; excellent free branching with or without pinching; intermediate vigor; responsive to B-9 to reduce internode length and peduncle elongation, and adaptability to pot sizes from 10 to 15 cm.

2 Drawing Sheets

The present invention relates to a new and distinctive cultivar of Kalanchoe plant, botanically known as *Kalanchoe blossfeldiana* Poelln., and referred to by the cultivar name Mandarin.

Mandarin, identified as 547-004, is a product of a planned breeding program which had the objective of creating new Kalanchoe cultivars for year-round commercial production having an earlier flowering response, well branched yet compact flowering plants, suitability for flowering in pots ranging from 10 to 15 cm, and having good flower and foliage keeping quality.

Mandarin was originated from a cross made by the inventor Margaret M. Fleming in a controlled breeding program in Half Moon Bay, Calif., in 1984.

The female parent of Mandarin was the cultivar identified as Durango, disclosed in U.S. Plant Pat. No. 5,667. The male parent was an unnamed seedling, identified as 402-119 produced from the crossing of Cinnabar and Fortyniner.

Mandarin was discovered and selected as one flowering plant within the progeny of the stated cross by Margaret M. Fleming in February of 1986 in a controlled environment in Soquel, Calif.

The first act of asexual reproduction of Mandarin was accomplished when vegetative cuttings were taken from the initial selection in July 1986 in a controlled environment in Soquel, Calif., by Margaret M. Fleming.

Horticultural examination of controlled flowerings of successive plantings has shown that the unique combination of characteristics as herein disclosed for Mandarin are firmly fixed and are retained through successive generations of asexual reproduction. Mandarin has not been observed under all possible environmental conditions. The phenotype may vary significantly with variations in environment such as temperature, light intensity and day length.

The following observations, measurements and comparisons describe plants grown in Soquel, Calif., under greenhouse conditions which approximate those generally used in commercial greenhouse practice.

The following traits have been repeatedly observed and are determined to be basic characteristics of Mandarin which, in combination, distinguish this Kalanchoe as a new and distinct cultivar:

1. Bright pumpkin-orange flower color.

2. Flower diameter of 16 to 18 mm at maturity.
3. Flowering response of from an early 9 weeks in summer to 11 weeks in winter after start of short days.
4. Very floriferous, with excellent display of many flowers.
5. Good keeping quality of both flowers and foliage, with each floret lasting up to two weeks under normal conditions of finishing and holding.
6. Branches freely with or without pinching.
7. Intermediate vigor.
8. Good responsiveness to B-9 to reduce internode length and peduncle elongation.
9. Proper scheduling makes this new cultivar suitable for production in 10 cm to 15 cm pots.

The accompanying colored photographic drawings show typical inflorescence and leaf characteristics of Mandarin, with colors being as nearly true as possible with illustrations of this type.

Sheet 1 is a color photograph of Mandarin grown as a non-pinched flowering Kalanchoe in a 10 cm pot.

Sheet 2 is a black and white photograph showing the leaves of Mandarin at three stages of development (mature, intermediate and immature).

Of the commercial cultivars known to the inventor, several may be compared to Mandarin in separate characteristics; in total no single commercial cultivar compares. Mandarin has similar flowering response to short days and similar plant habit and growth characteristics as the cultivar identified as Flamboyant, disclosed in U.S. Plant Pat. No. 5,875. However, the orange flower color of Mandarin in much brighter and more orange than the gold-orange flower color of Flamboyant, and Mandarin has better keeping quality of both flowers and foliage than Flamboyant.

The flower color of Mandarin may be compared to the flower color of the cultivar identified as Tropicana, disclosed in U.S. Plant Pat. No. 5,961. However, the flowering response of Mandarin is three to four weeks earlier than the flowering response of Tropicana. Also, Mandarin is more vigorous than Tropicana, and has larger flowers and a larger display of more flowers than Tropicana.

In comparison to the female parent Durango, Mandarin has similar flower color and foliage. However, Mandarin has a more compact plant habit and has an earlier flowering response by two to three weeks than Durango.

Mandarin can also be compared to the male and female grandparents, Cinnabar and Fortyniner, respectively. With respect to Cinnabar, the flower color of Mandarin is a bright pumpkin orange, contrasted to the red/orange flowers of Cinnabar. The keeping quality of both the flowers and foliage of Mandarin is superior to Cinnabar. The flowers of Mandarin will last up to two weeks and the plant looks good for a month or more. The flowers of Cinnabar last 7–10 days, and the plant fades faster than Mandarin. The growth characteristics and flowering response of both cultivars are similar.

When compared to Fortyniner, the flower color of Mandarin is a bright pumpkin orange, compared to the yellow flower color of Fortyniner. A further significant difference is in the flowering response, with Mandarin flowering two weeks earlier both in winter and summer. In addition, the keeping quality of both the flowers and foliage of Mandarin is substantially better. The inflorescence of Mandarin is more vertical which results in the fading flowers being concealed by the bright newly opened flowers. This, in addition to the longer keeping quality, provides a plant having a continuous and relatively uniform display of flowers. Fortyniner tends to flower in a longer sequence, and the inflorescence is more horizontal. This produces a display in which buds, open flowers, fading flowers, and spent flowers all appear, thereby detracting from the entire display. In addition, the foliage of Fortyniner is relatively short-lived. By the time the plant is flowering, the lower leaves are normally degrading or gone entirely.

In the following description color references are made to The Royal Horticultural Society Colour Chart. The color values were determined on plant material grown as a non-pinched pot plant in a 10 cm pot in Soquel, Calif., on Oct. 23, 1988.

Classification:

*Botanical.*—*Kalanchoe blossfeldiana* Poelln. cv. Mandarin.

*Commercial.*—Flowering pot Kalanchoe.

Parentage:

*Female parent.*—Durango (U.S. Plant Pat. No. 5,667).

*Male parent.*—An unnamed seedling (402-119).

Propagation:

(A) *Type cutting.*—Short tip cutting, with stems up to 2 cm.

(B) *Time to root.*—10 days at 21° C. in summer; 14 days at 21° C. in winter.

(C) *Rooting habit.*—Many very fine roots, fibrous.

Plant description:

(A) *Form.*—Intermediate, upright growth. Growing and scheduling practices can produce a small plant in a 10 cm pot up to a larger plant in a 15 cm pot.

(B) *Habit of growth.*—Rate of growth moderate for this type of plant. Generally, shoots are formed at every node, with internodes being 12–25 mm for a vegetative natural plant; height of plant above a 10 cm pot is approximately 15–25 cm, based on 2 to 3 applications of 3500 ppm B-9 SP growth regulator.

(C) *Foliage description.*—Leaves simple, opposite, slightly lobed. 1. Size: Average full grown leaf in a 10 cm flowering pot is 110 mm long×80 mm wide. 2. Shape: Ovate to elliptic, apex obtuse to slightly pointed, base attenuate. 3. Texture: Glabrous, coriaceous, succulent. 4. Margin: Sinuate to crenate. 5. Color (mature foliage): Upper surface 147A; under surface 147B. 6. Durability: Excellent; no degradation observed even on the lower foliage of plants retained for months beyond normal expectancy. 7. Foliar diseases: Resistant or immune to Powdery Mildew. Chlorosis, stem rot and root rot have not been observed. Mandarin may under some conditions exhibit a minute necrotic spot at the tip of the lower leaves, a trait shared with Durango, the female parent. It does not get larger, nor spread, and does not substantially detract from the total plant.

Flowering description:

(A) *Flowering habit.*—Inflorescence of each shoot is formed by dichotomous branching, starting with opening of terminal flower of main axis, followed by terminal flowers of the side branches, continuing with subsequent development of branches in the inflorescence. Opening of new buds (12–17 mm) will continue for two months or more. Individual flowers last two weeks or more after opening. No fragrance perceived.

(B) *Flowering response.*—Flowering time under controlled day length after start of short days is 9 weeks in summer to 11 weeks in winter.

(C) *Flowers borne.*—Compound dichasial cymes; peduncle length 5–12 cm, diameter 4–8 mm; pedicel length 5–7 mm, diameter greater than 1 mm.

(D) *Quantity of flowers.*—Very floriferous; floret count 80–90 per primary inflorescence, 400 or more total per 10 cm pot plant, commercial culture.

(E) *Petals.*—1. Shape: Slightly pointed to almost round. 2. Color: Upper surface: 30C to 30D. Under surface: 20B to 20C, slightly streaked with 30D. 3. Number of petals: 4, united in corolla. 4. Flower diameter: 16 to 18 mm at maturity.

(F) *Reproductive organs.*—1. Stamens: 8 in number. a. Anther shape: Flat, elliptical, color yellow. b. Filament color: Light green. c. Pollen color: Yellow. 2. Pistils a. Stigma shape: Flat, crystalline, color greenish white. b. Style color: Light green. c. Ovaries: 4-celled, color light green.

(G) *Flower diseases.*—None noted to date. Resistant to Botrytis; no problems with fading or color breaking.

I claim:

1. A new and distinct Kalanchoe plant named Mandarin, as described and illustrated.

* * * * *

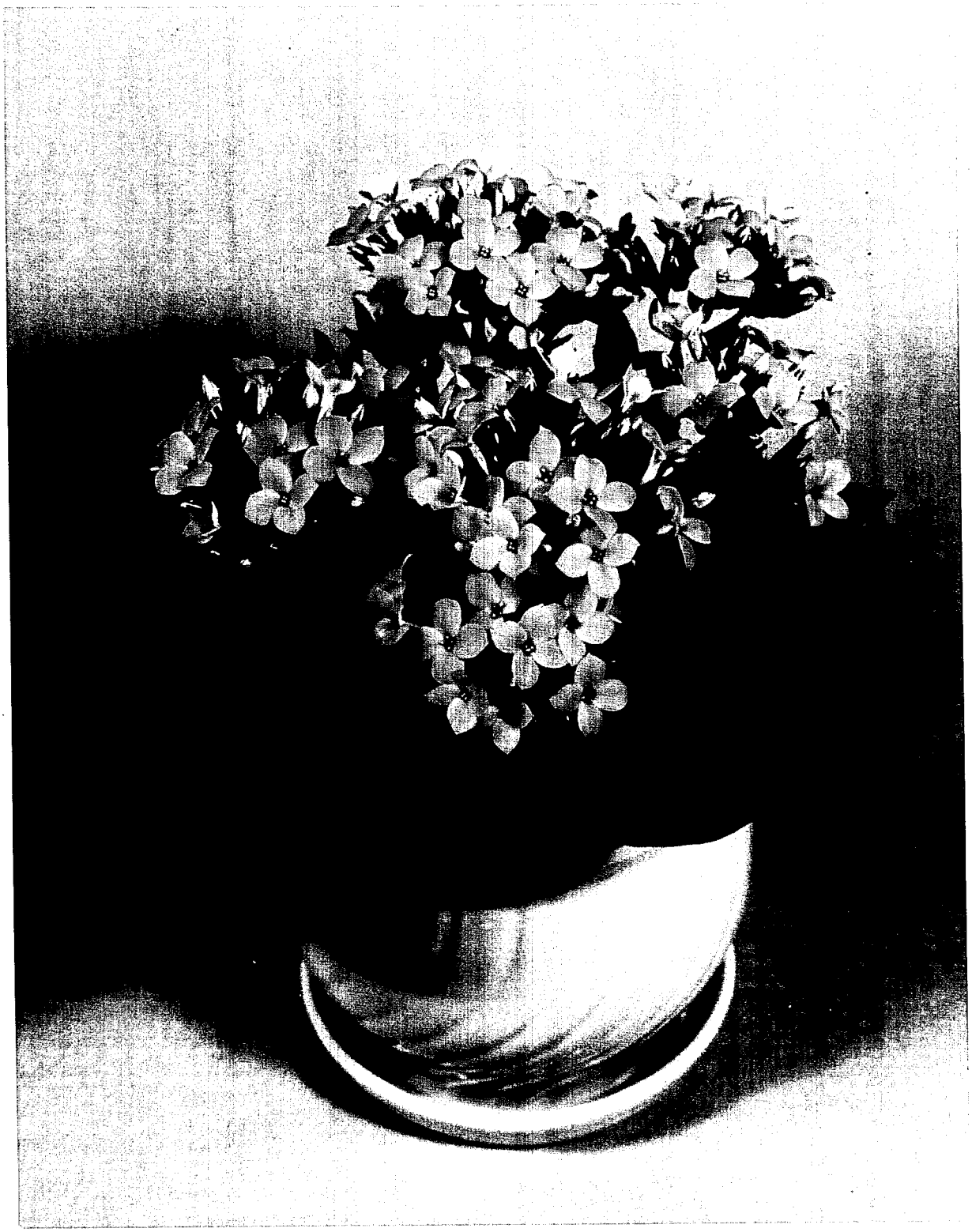

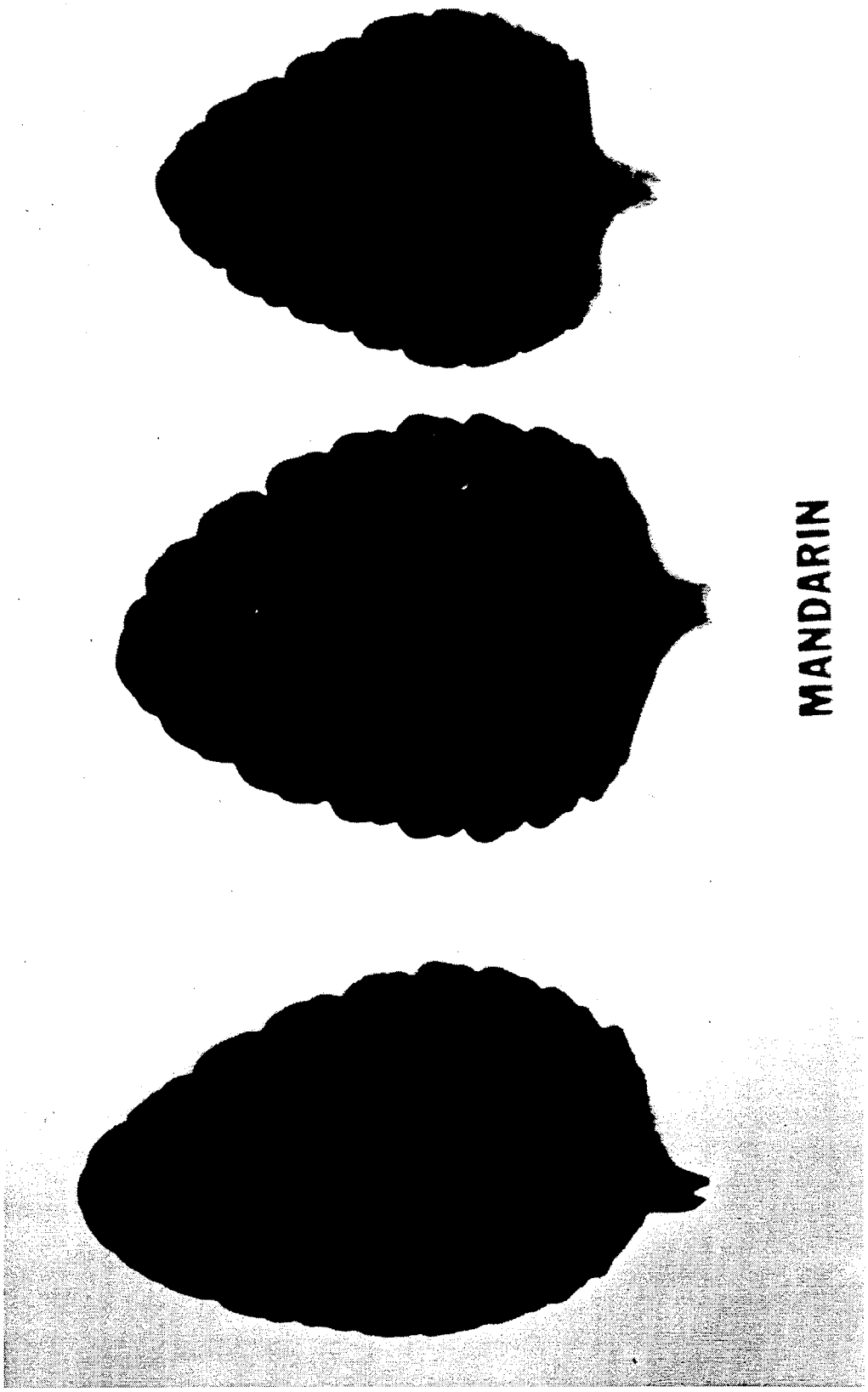
MANDARIN